United States Patent
Blanchard et al.

(10) Patent No.: US 10,092,633 B2
(45) Date of Patent: Oct. 9, 2018

(54) NEWLY IDENTIFIED PEPTIDES FOR USE IN THE INDUCTION OF ORAL TOLERANCE IN YOUNG MAMMALS

(71) Applicant: NESTEC S.A., Vevey (CH)

(72) Inventors: Carine Blanchard, Le Mont-sur-Lausanne (CH); Sophie Nutten, Palezieux-Village (CH); Alexandre Panchaud, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/105,123

(22) PCT Filed: Dec. 16, 2013

(86) PCT No.: PCT/EP2013/076643
§ 371 (c)(1),
(2) Date: Jun. 16, 2016

(87) PCT Pub. No.: WO2015/090347
PCT Pub. Date: Jun. 25, 2015

(65) Prior Publication Data
US 2016/0375114 A1 Dec. 29, 2016

(51) Int. Cl.
| | |
|---|---|
| *A61K 38/00* | (2006.01) |
| *A61K 39/00* | (2006.01) |
| *A61K 38/01* | (2006.01) |
| *A61K 38/08* | (2006.01) |
| *A23L 33/18* | (2016.01) |
| *A23L 33/00* | (2016.01) |
| *A61K 35/747* | (2015.01) |

(52) U.S. Cl.
CPC .......... *A61K 39/001* (2013.01); *A23L 33/18* (2016.08); *A23L 33/40* (2016.08); *A61K 35/747* (2013.01); *A61K 38/018* (2013.01); *A61K 38/08* (2013.01); *A23V 2002/00* (2013.01); *A61K 2039/54* (2013.01); *A61K 2039/545* (2013.01); *A61K 2039/577* (2013.01)

(58) Field of Classification Search
None
See application file for complete search history.

(56) References Cited

U.S. PATENT DOCUMENTS

| | | | | |
|---|---|---|---|---|
| 2006/0286208 | A1* | 12/2006 | Rangavajla | A23J 3/34 426/34 |
| 2013/0344042 | A1* | 12/2013 | Tanbonliong | A61K 35/747 424/93.45 |

FOREIGN PATENT DOCUMENTS

| | | |
|---|---|---|
| EP | 0629350 | 12/1994 |
| EP | 2332428 | 6/2011 |
| RU | 2192884 | 11/2002 |
| WO | 0042863 | 7/2000 |
| WO | 2007004876 | 1/2007 |
| WO | 2012075570 | 6/2012 |

OTHER PUBLICATIONS

Picariello et al. "Peptides surviving the simulated gastrointestinal digestion of milk proteins: Biological and toxicological implications" Journal of Chromatography B, 2010, vol. 878, pp. 295-308.
Cocco et al. "Mutational analysis of immunoglobulin E-binding epitopes of β-casein and β-lactoglobulin showed a heterogeneous pattern of critical amino acids between individual patients and pooled sera" Clinical and Experimental Allergy, 2007, vol. 37, pp. 831-838.
Totsuka et al. "Fine mapping of T-cell determinants of bovine β-lactoglobulin" Cytotechnology, 1997, vol. 25, pp. 101-113.
Abstract of JP Application No. 2001:289974, Entitled "Blood Cholesterol-Lowering Peptides", 2 pages, XP002724054.
Russian Office Action for corresponding application 2016128923/10(045069), dated Feb. 28, 2018, 8 pages.

* cited by examiner

*Primary Examiner* — Christina Bradley
(74) *Attorney, Agent, or Firm* — K&L Gates LLP

(57) ABSTRACT

The invention relates to newly identified peptides of that are capable of inducing tolerance to cow's milk, especially to β-lactoglobulin. The peptides may be administered to mammals, especially to young infants who are at risk of allergy to cow's milk proteins, to induce oral tolerance to cow's milk; they may also be administered to children or adults who are allergic to cow's milk to allow "desensitization" towards the allergenic milk proteins, especially β-lactoglobulin, to occur. The peptides may also be used to induce tolerance to goat's and buffalo's milk proteins, especially β-lactoglobulin. The peptides are capable of modulating the mammalian immune response to allergens.

18 Claims, 1 Drawing Sheet
Specification includes a Sequence Listing.

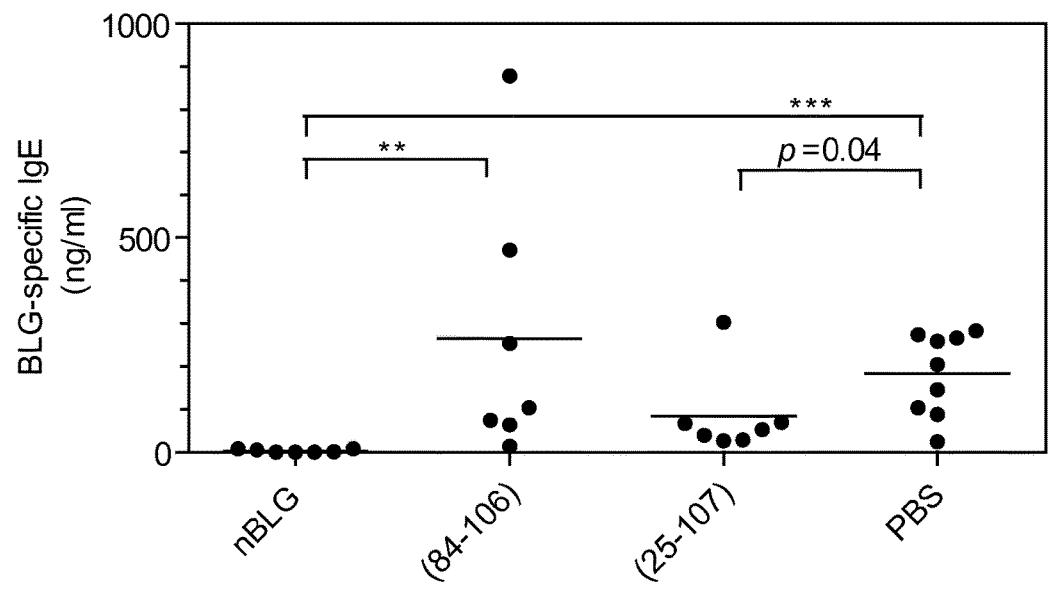

NEWLY IDENTIFIED PEPTIDES FOR USE IN THE INDUCTION OF ORAL TOLERANCE IN YOUNG MAMMALS

CROSS REFERENCE TO RELATED APPLICATIONS

The present application is a National Stage of International Application No. PCT/EP2013/076643, filed on Dec. 16, 2013, the entire contents of which are being incorporated herein by reference.

FIELD OF THE INVENTION

This invention relates to newly identified peptides of β-lactoglobulin that are hypoallergenic, but retain the capability to induce tolerance to the native protein. The peptides may be administered to all infants, especially those who are at risk of allergy to cow milk proteins, specifically β-lactoglobulin. The peptides are capable of modulating the infant immune response to allergens.

BACKGROUND TO THE INVENTION

Cow's milk allergy (CMA) affects approximately 2.5% of all infants and is considered the most common food allergy in this age group [Sicherer S H et al. (2010), Food allergy, Sampson H A, *J. Allergy Clin. Immunol.* (125)]. Approximately 85% of children out-grow their allergy to cow's milk before the age of 2 to 3 years old. As such, CMA affects other age groups with a lower prevalence.

The allergies to cow's milk and to the formulas containing cow's milk adapted to the needs of infants are due to the fact that the proteins of cow's milk differ from the proteins of mother's milk and can constitute allergens.

Besides breastfeeding, the primary recommendation for prevention of CMA is the use of partially hydrolyzed hypoallergenic formulae, which are recommended to be prescribed to "at risk" asymptomatic infants, with atopic parents.

In contrast to standard infant cow's milk formulae, in hypoallergenic formulae, the cow's milk proteins have been hydrolyzed, to decrease their potential allergenicity. This approach has been demonstrated to be efficient to prevent sensitization by native (full length) proteins present (albeit in a much lower quantity than that in a non-hydrolyzed formula) in the formulae.

Hydrolysates may be characterized as "partial" or "extensive" depending on the degree to which the hydrolysis reaction is carried out. Currently, there is no agreed legal/clinical definition of Extensively Hydrolyzed Products according to the WAO (World Allergy Organization) guidelines for CMA, but there is agreement that according to the WAO hydrolyzed formulas have proven to be a useful and widely used protein source for infants suffering from CMA. In the current invention a partial hydrolysate is one in which 60% of the protein/peptide population has a molecular weight of less than 1000 Daltons, whereas an extensive hydrolysate is one in which at least 95% of the protein/peptide population has a molecular weight of less than 1000 Daltons. These definitions are currently used in the industry.

There are currently many examples of casein or whey-based hypoallergenic partially or extensively hydrolyzed formulae (e.g. NAN-HA™, also known as BEBA-HA™, Alfare™, Altéra™ from Nestlé, and S26-HA™ from Pfizer) on the market.

For infants already displaying symptoms of CMA, non-allergenic milk substitute formulae, such as free amino acids (e.g. Vivonex™ from Nestlé) or soy based formulas (such as S-26 Soy™, NURSOY™ from Pfizer, New York, and NESTLÉ® Good Start® ALSOY® from Nestlé) may be suitable alternatives to cow's milk standard or hypoallergenic formulae.

Thus, the primary focus to date in providing nutrition for children with allergies to cow's milk has been to find preparations which will not induce an allergic response, i.e. to provide non-allergenic formulations. One of the drawbacks of administering non-allergenic formulae (containing either free amino acids, soya based milk or extensively hydrolyzed cow's milk proteins) to infants is that, while such formulations allow infants who are allergic to cow's milk to avoid an allergic response, they do not allow those children to develop oral tolerance to the cow's milk protein allergens so that they can go on to drink unaltered milk products later in life.

Oral tolerance is the specific suppression of cellular and/or humoral immune reactivity to an antigen by prior administration of the antigen by the oral route. It is an important part of the development of the immune system in the first months of life and allows the infant to consume food without adverse reaction. Failure of the establishment of oral tolerance leads to allergy. The development of oral tolerance is linked to the normal immune system education, resulting in a reduced reaction to food antigens.

Several factors have been identified as affecting the induction and maintenance of oral tolerance, among these, the structure of the food protein, the dose and frequency of the antigen administration, as well as the immune status of the host.

It is believed that some peptides, that may be specifically present in partially hydrolyzed infant formula, have the ability to interact with the immune system and induce oral tolerance.

It has been found that partially hydrolyzed milk formulations are not only of reduced allergenicity but can induce immunological tolerance to milk proteins (EP 0827 679).

Thus, European patent application EP 2 332 428 discloses a formulation comprising a cow's milk peptide-containing hydrolysate capable of inducing oral tolerance. The peptides in question were identified as coming from bovine casein.

WO 00/42863 describes the identification of a number of tolerogenic peptides of β-lactoglobulin (one of the major cow's milk allergens) capable of inducing oral tolerance, as evidenced by reduced immune responses (IgE) to the native protein in mice previously exposed to the peptides in question, compared to mice that had not been exposed to the peptides. In that patent application, the authors refer to EP 0 629 350, which discloses the use of non-allergenic whey protein hydrolysates which are said to be capable of inducing cow's milk protein tolerance. The authors of WO 00/42863 indicate that although in EP 0 629 350 it was stated that whey protein hydrolysates substantially free of allergenic proteins could be used to induce cow's milk protein tolerance in children at risk of cow's milk allergy, they found, on analyzing other non-allergenic whey protein hydrolysates, that non-allergenicity did not necessarily translate into the ability to induce cow's milk protein tolerance. They went on to say that even some of the formulations exhibiting the highest degree of non-allergenicity were found to be unsuitable for inducing cow's milk protein tolerance.

Furthermore, it is known that extensively hydrolyzed formulae lose their ability to induce long-term oral tolerance, i.e. the hydrolysis modifies extensively the nature of the protein in a way that it is no longer recognized by the immune system. This leads to the loss of a critical benefit.

Thus, there is a need to further identify the factors that may influence induction of oral tolerance. It is highly desirable to provide hypoallergenic or non-allergenic compositions to be used as a complement to or substitute for breast milk and having an ability to induce oral tolerance in the infant.

There is a need to provide synthetic nutritional solutions that can alleviate the development of allergies, especially in infants. There is a need to induce tolerance to a variety of allergens including milk allergens and milk proteins.

There is a need to design and produce nutritional interventions, especially via synthetic ingredients or combinations of ingredient, that can be administered to infants early in life and that reduce the probability or the magnitude of being or becoming allergic or developing allergies later in life.

This need exists for the general population of infants and also for sub-populations of infants having predisposition to allergies or having declared allergies.

There is a general need to provide relief from allergies or allergy symptoms and to develop means of inducing the tolerance to common allergens, such as milk allergens, especially in children and infants.

SUMMARY OF THE INVENTION

This invention provides newly identified peptides, SEQ ID No.1 to SEQ ID No.5, of β-lactoglobulin (BLG) for the induction of tolerance to milk proteins in individuals at risk of protein allergy, as well as those already suffering from allergy. The newly identified peptides SEQ ID No.1-5 are recognized by and bind to HLA-DR (Human Leucocyte Antigen-DR). Thus, each of these peptides contains a HLA epitope, which facilitates recognition by the immune cells and induction of oral tolerance towards milk proteins, especially β-lactoglobulin (BLG) in mammals. The milk protein may be from cow, sheep, goat or buffalo.

Thus, the invention concerns a peptide or combination of peptides having an amino acid length of from five to twelve amino acids and comprising a sequence chosen from SEQ ID No.1-5, for the induction of oral tolerance to milk proteins from cow, sheep, buffalo or goat in mammals. Human infants are especially concerned.

For an enhanced tolerogenic effect, one or more peptides having a length of from five to twelve amino acids, and comprising one of the sequences a, b and c in Table 1, may be administered in combination with the peptide or combination of peptides based on SEQ ID No. 1-5, described in the previous paragraph.

The peptides may be administered in their pure form; diluted in suitable liquid, or in the form of a pharmaceutical composition, a nutritional composition or nutritional supplement.

According to an embodiment of the invention the peptides are in the form of (i) isolated peptidic fractions from the hydrolysis of proteinaceous material containing BLG, and/or (ii) synthetically prepared peptides.

A major advantage of these peptides is to induce oral tolerance to cow, sheep, buffalo or goat milk proteins, in particular to β-lactoglobulin, in mammals. These mammals may be young mammals, and particularly human infants, "at risk" of developing cow's milk allergy, having at least one parent or sibling who is allergic to cow's milk, or not "at risk". Thus, the peptides of the invention are of benefit to the general population of young mammals. Another group that may benefit from the administration of the peptides of the invention is adult mammals who are already allergic to cow's milk. Thus, the allergic adult may be "desensitized" to the native allergen after exposure to the tolerogenic peptides of the invention. Thus, one or more (two, three, four, or all five) of the peptides may be administered to the mammal to induce oral tolerance to milk proteins, especially BLG.

The peptides may be administered to pets, for example dog and cats.

These peptides represent an advantage compared to the previously identified peptides (see Table 1 peptides a, b, c) from BLG (see WO 0042863). Upon exposure to BLG, peptides 2-5 down-regulate the expression of IgE to a greater extent (see FIG. 1) than do the previously identified peptides, a, b and c (see FIG. 1).

In a preferred embodiment, the peptide or combination of peptides is in the form of peptidic fraction comprising at least one of the peptides SEQ ID No.1 to SEQ ID No.5. The peptide or combination of peptides may be administered to the young mammal, or adult mammal at a dose of between 0.4-50 umol/per kg bodymass/day, preferably from 0.9-40 umol/per kg bodymass/day. The administration may be every day, or every second day, or every third day, or once a week for a period of at least two weeks, preferably at least one month, more preferably at least three months. The administration may be for longer, for example up to three years.

A "one-shot" administration may be effective inducing oral tolerance to BLG in subjects who have not yet been exposed to BLG.

The peptides may be administered in a composition comprising between 25-250 ug peptide per gram of dry composition, preferably between 50-150 ug peptide per gram of dry composition. The peptides may be added to a base composition that is a starter infant formula, or a follow-up infant formula or a growing up milk. The base composition may be a "non-allergenic" or hypoallergenic composition.

The peptides may be administered in a composition comprising further ingredients or prebiotics, preferably selected from inulin, fructooligosaccharide (FOS), short-chain fructooligosaccharide (short chain FOS), galacto-oligosaccharide (GOS), xylooligosaccharide (XOS), glanglioside, partially hydrolyzed guar gum, acacia gum, soybean-gum, or mixtures thereof.

The peptides may be administered in a composition comprising further ingredients or probiotics, preferably selected from *Lactobacillus paracasei, Lactobacillus GG, Lactobacillus rhamnosus, Bifidobacterium longum, Bifidobacterium lactis*, and *Bifidobacterium breve*.

BRIEF DESCRIPTION OF THE DRAWINGS

FIG. 1: β-lactoglobulin (BLG) specific humoral immune responses in mice gavaged with native β-lactoglobulin (nBLG) or synthetic peptides and then experimentally sensitized.

Mice were gavaged with nBLG or synthetic peptides and then experimentally sensitized with nBLG. BLG-specific IgE (A) antibodies were quantified on individual sera collected on day 30. Statistical significance between specified groups using Kruskall-Wallis and Dunn's Multiple comparison post-test are indicated (* $p<0.05$,  $0.01<p<0.001$, * $p<0.001$).

DETAILED DESCRIPTION

In the present invention, the term "tolerance" is to be understood as a state of specific immunological unresponsiveness. Both humoral (antibodies) and cell-mediated (lymphocyte etc.) pathways of the immune response may be suppressed by tolerance induction. A breakdown of oral tolerance is considered to be the underlying cause of food allergy.

The term "allergen" is to be understood as a protein or macropeptide capable of initiating allergic reactions in mammals, particularly in "at risk" young mammals, including infants or nurslings. Young infants are considered being "at risk" of protein allergy when either at least one parent or sibling is atopic.

The term "tolerogenic peptides" is to be understood as proteic fragments, corresponding to parts of the native protein, sized from 200 to 6000 Da (3 to 50 amino acids), and preferably between 500 to 3000 Da, and more preferably between 500 and 1400 Da and being able to induce specific oral tolerance to native proteins.

The term "non-allergenic" base composition is to be understood as a composition having a nitrogen source containing a well-balanced amino-acid composition. The "non-allergenicity" is defined for milk proteins as residual allergenicity of individual whey proteins not exceeding 1 ppm and as residual allergenicity of total caseins not exceeding 10 ppm.

The term "sensitization" means induction/development of allergen-specific IgG1 and/or IgE antibodies.

The current invention relates to a number of newly identified peptides, and their use for the induction of oral tolerance to cow's milk protein, in particular, to β-lactoglobulin, in the general population of young mammals, including those considered "at risk" of developing CMA and those who are not as well as in adult mammals who are allergic to cow's milk. The newly identified peptides may also induce oral tolerance to BLG from sheep, goat or buffalo, as they are also found in sheep, goat and buffalo milk.

The peptides of the current invention have an amino acid length of from five to twelve and comprise a sequence chosen from SEQ ID No.1-5 (see Table 1). The peptide thus, has a specific length (5-12 amino acids).

Peptides shorter than pentamers (five amino acids in length) may not provide the tolerogenic effect, whereas peptides that are longer than 12-mers are thought to have an increased risk of allergenicity.

Thus, the peptide may be a 5-mer, 6-mer, 7-mer, 8-mer, 9-mer, 10-mer, 11-mer or a 12-mer comprising any one of the sequences selected from SEQ ID No. 1-5. Thus, the peptide may be any peptide that is a 5-mer, 6-mer, 7-mer, 8-mer, 9-mer, 10-mer 11-mer or a 12-mer comprising the sequence IIAEK (Seq ID No. 1) or IVTQTM (Seq ID No. 1), or KGLDIQK (Seq ID No. 2), or DAQSAPLR (Seq ID No. 3), VEELKPTPE (Seq ID No. 4) or IIAEK (Seq ID No. 5).

Similarly, peptides that may provide an enhanced effect when administered with the above described peptides based on sequences SEQ ID No. 1-5, are any peptides that are a 5-mer, 6-mer, 7-mer, 8-mer, 9-mer, 10-mer, 11-mer or a 12-mer, and comprise any one of the sequences selected from a, b and c in Table 1.

Thus, the peptides of the invention induce oral tolerance to milk proteins from cow, sheep, buffalo or goat in mammals.

Preparation and Characterization of the Peptides

According to one embodiment of the invention, the isolated peptides may be synthetically made, according to standard methods known to the skilled person. Alternatively, according to another embodiment of the invention they may be concentrated, extracted and/or siloed from natural sources such as milk (e.g. bovine milk) or milk fractions which have been preferably modified, treated to, for example, produce or concentrate the peptides. Milk hydrolyzates, in which milk proteins have been hydrolyzed by enzymes or other means, may be generated by methods known in the art. Methods for extracting, separating and identifying the peptidic fractions containing the peptides of the invention, from milk hydrolyzates are also known to the skilled person. The peptides of the invention may be generated by these methods.

For example, the peptides of the invention may be produced using a method disclosed in U.S. Pat. No. 5,039,532A. The enzymatic hydrolysis process includes a two-step hydrolysis reaction with a heat denaturation step in between to ensure that the final hydrolysate is substantially free of intact allergenic proteins. For example, trypsin and chymotrypsin may be used in these methods and may be preparations produced by extraction of porcine pancreas, or produced by recombinant DNA technology in bacteria.

For example, the enzymatic hydrolysis may be carried out using any of a whey starting material containing whey proteins. This starting material may be a whey from cheese making, particularly a sweet whey such as that resulting from the coagulation of casein by rennet, an acidic whey from the coagulation of casein by an acid, or the acidifying ferments, or even a mixed whey resulting from coagulation by an acid and by rennet. This starting material may be whey demineralized by ion exchange and/or by electrodialysis. This whey may be a concentrate of whey proteins more or less free from lactose obtained, for example, by ultrafiltration optionally followed by dialysis. The starting material may even be a combination of the above-mentioned starting materials and lactose. It may be in the form of a true or colloidal aqueous solution or in the form of a powder. In the latter case, the powder is dissolved in preferably demineralized water to form an aqueous solution.

The starting material is subjected to enzymatic hydrolysis in known manner using mixed or purified proteolytic enzymes active in the basic and neutral ranges, for example trypsin, chymotrypsin or pancreatin. The preliminary hydrolysis may be carried out for a relatively short time, preferably 5 to 35 minutes, for example 10 minutes, using a small quantity of enzyme, for example 10% of the total quantity used for the hydrolyses. This enables quantities of enzyme used to be economized. In this case, hydrolysis is partial. This hydrolysis may be carried out in a reactor or, alternatively, in a tube.

In cases where the substrate to be hydrolyzed might tend to coagulate during the heat treatment, a chelating agent, such as calcium or magnesium citrate for example, may be added to the substrate, as indicated, for example, in U.S. Pat. No. 4,748,034. The hydrolyzate is subjected to a heat treatment at 80° to 100° C. for 3 to 10 minutes at a pH value of 6 to 8. The heat treatment time and temperature are of course interrelated, the lower temperature limit corresponding to the upper time limit and vice versa. In industrial heat exchangers, a temperature of approximately 90° C. and a residence time of the order of 5 minutes have proved to be sufficient for denaturing the minor proteins. It has, in effect, been found that denaturing these proteins makes them accessible to the subsequent enzymatic degradation. It is advisable to mention that the heat treatment inactivates the enzyme.

The hydrolyzate is then cooled to a temperature of 40° to 60° C. and preferably to a temperature of approximately 55° C., which is the optimal temperature for the hydrolytic activity. The pH value is preferably adjusted to approximately 7.5 by addition of an aqueous solution of a base. The conditions of the second hydrolysis may vary. For example, it may be carried out discontinuously in batches in a thermostatically controlled tank reactor. After addition of the proteolytic enzyme selected from trypsin, chymotrypsin, pancreatin or a mixture of trypsin and chymotrypsin in aqueous solution, the hydrolysis is carried out for 60 to 180 minutes.

Otherwise, the second hydrolysis may take place continuously for 1 to 60 minutes, and preferably for 2 to 20 minutes in a tube which constitutes the turbulent-state reactor. In this variant, the tube, depending on its length, provides the reaction time required according to the throughput of product to be hydrolyzed. Accordingly, the enzyme has to be pumped continuously to the entrance of the dwell tube. The resulting state of high turbulence brings about rapid and intense contact between the enzyme and the substrate. Irrespective of the mode employed (batch or continuous) selected for the second hydrolysis, the hydrolysis product undergoes a heat treatment which inactivates the enzyme. This heat treatment comprises preheating the hydrolyzate to a temperature of or above 75° C. and keeping it at that temperature (preferably at 75° to 85° C.) for about 5 minutes to promote auto-digestion of the enzyme, this treatment advantageously being followed by sterilization, preferably at ultra-high temperature, for example at 125° to 135° C., for 2 to 3 minutes by injection of steam or in a heat exchanger. The hydrolyzate may then be dried, for example by spray drying or by freeze drying for different applications, or may even be subsequently treated. In the latter case, the enzyme may be inactivated during the subsequent treatment.

Identification and Characterization of the Peptides

In a set of experiments detailed in Example 1, the present inventors identified the peptide sequences of BLG responsible for the induction of oral tolerance towards milk proteins, in particular BLG. In a first step, using a cellular based assay, partially hydrolyzed infant formula NAN HA™ (otherwise known as BEBE HA™) from Nestlé, was incubated with human cells expressing the Major Histocompatibility Complex (MHC) class II receptor, HLA-DR. As the first step in the induction of oral tolerance, the HLA receptor presents peptide sequences to the T cells, thereby inducing tolerance. Thus, development of tolerance is largely dependent on the recognition of the peptide sequence by the MHC.

The peptide binding regions of the MHC recognize peptide sequences or assembly of peptides composed of, on average, ten amino acids with a minimum number of five. Indeed, these penta-peptides can be included in longer peptide sequences (or even proteins), as they will be digested in the gastrointestinal tract to lead to this smaller peptide size of 5-18 amino acids. This explains, in part, why extensively hydrolyzed products, composed of free amino acids, di-peptides, tri-peptides, and tetra-peptides do not induce oral tolerance.

Thus, in the current invention, the human cells expressing HLA-DR were cultured in the presence of NAN-HA™ formula (which had been verified to be non-toxic for the cells), the peptides that bound to the HLA receptor were isolated by immunoprecipitation, and then identified by mass spectrometry and amino acid sequencing.

The newly identified peptides are from BLG and are listed in Table 1.

| SEQ ID No. | Sequence | Position in BLG Sequence |
|---|---|---|
| 1 | IVTQTM | 18-23 |
| 2 | KGLDIQK | 24-29 |
| 3 | DAQSAPLR | 49-56 |
| 4 | VEELKPTPE | 59-67 |
| 5 | IIAEK | 87-91 |
| a | IDALNENK | 100-107 |
| b | VLDTDY | 110-115 |
| c | EVDDEALEK | 143-151 |

Peptides a, IDALNENK, b, VLDTDY, and c EVDDEALEK were also identified by this method. These peptides were previously identified in WO 20042863 as being inducers of oral tolerance. The peptides were identified as part of a longer peptide sequence in the latter document. Thus, these known peptides act as a positive control in the current experiment.

The Tolerogenic Nature of the Peptides Evidenced in vivo

The ability of these peptide sequences to induce oral tolerance in vivo was further assessed in an experimental mouse model of sensitization to BLG (see Example 2 and FIG. 1).

This animal model has previously been used to demonstrate the efficiency native BLG in tolerance induction after gavage [Patient, Ket et al., (2011). Oral tolerance and Treg cells are induced in BALB/c mice after gavage with bovine β-lactoglobulin. Allergy, 66 (10), 1312-1321]. Interestingly, in the latter article, it was demonstrated that BLG that had been subjected to trypsin hydrolysis did not induce oral tolerance.

The mouse model was used to measure oral tolerance induction for full length native BLG, and two synthetic peptides of BLG, corresponding to the sequences (84-106) and (25-107) of bovine BLG. Mice were fed either native BLG or either synthetic peptide (84-106) or (25-107) by gavage on day 1, 2, 3, 8, 9 and 10. They were then sensitized by i.p. administration with native BLG on day 14. Serum IgE levels were measured between day 30 and 33.

FIG. 1 demonstrates that gavage with native BLG induces an efficient tolerance, preventing further induction of BLG-specific IgE production upon sensitization with BLG. The peptide (25-107) which contains sequences 2, 3, 4, 5 of the invention, as well as previously known peptide a, leads to a reduction in serum IgE levels compared to the control (PBS) (p=0.04). The peptide (84-106), comprising sequences 5, a, b, and c demonstrates a tendency towards a lower level of IgE compared to PBS.

The inventors conclude that the peptides 1-5, which were derived from sequence (25-107), are more effective in inducing oral tolerance in this mouse model than those (a, b and c) derived from sequence (84-106). These longer peptide sequences (25-107) and (84-106), once gavaged in the mice, are naturally processed by pancreatic enzymes and proteases thus leading to the production of smaller peptides, including the sequences SEQ ID No.1-5 and sequences a, b and c.

The experiment demonstrates that the newly identified peptides 1-5 are recognized by, and bind to HLA-DR. These peptides may then be presented to the T cells. This process allows the induction of oral tolerance to the allergenic protein containing these sequences, i.e. BLG. The peptide or combination of peptides 1-5 according to the present invention, have been selected for their ability to induce oral tolerance.

According to a embodiment of the invention, the peptide or combination of peptides administered for the induction of oral tolerance is chosen from sequences SEQ ID No.1-5.

It is speculated that the tolerogenic effect produced by peptides is intensified when administered in combination with one or more of peptides chosen from the known peptides a, b and c in Table 1. This combination is expected to provide an enhanced effect in the induction of oral tolerance to BLG, relative to the effect induced by either peptide group a, b, c or 1-5, taken alone.

Thus, according to an embodiment of the invention, a peptide or a combination of peptides chosen from SEQ ID No.1-5 is administered in combination with peptides a, b and c.

Sequences SEQ ID No.1-5 have been identified as being highly conserved (100% sequence identity) in BLG in the following species: cow, buffalo, domestic goat, sheep and mouflon. Thus, it is believed that any of these sources of milk containing these sequences can induce oral tolerance to bovine milk and vice versa. Thus, the inventors postulate that peptides identified by the inventors can induce oral tolerance to BLG from any of these sources. In many countries, goat's and sheep's milk are consumed as an alternative or in addition to cow's milk. There are infant formulas on the market that use goat milk whey as a protein source. Thus, the application of the present findings to milk from species other than cow may be of interest.

According to one embodiment of the invention, the peptide or combination of peptides is administered in an amount sufficient to induce oral tolerance, preferably complete oral tolerance to bovine BLG. The BLG may also be from sheep, or goat. Complete oral tolerance is taken to mean no allergic reaction is observed after a DBPCFC (double blind placebo controlled food challenge) performed with cow's milk, in particular bovine BLG.

According to one embodiment of the invention, the peptides may be present in an amount of 0.01% to 5%, and preferably 0.1% to 0.5% of total protein.

According to one embodiment of the invention, the combination of peptides comprises one or two or three or four or more peptides.

The peptide or combination of peptides may be administered orally directly to the young mammal alone (pure or diluted in water or mother's milk, for example) or as a composition that is an infant milk formula or a food supplement, for example, a human milk fortifier. It may also be administered in any milk support used during trophic feeding, non-milk based infant formulas, a baby cereal or yoghurt, a baby meal pudding of cheese, a dairy or fruit drink, a smoothy, a snack or biscuit or other bakery item. The peptide or combination of peptides may be administered to adults in the form of a drink, food or food supplement. It may also be administered in pet food and beverage such as any dry food or kibble, wet food or canned form, or supplement.

Synthetic peptides and/or peptides concentrated by artificial means may be part of man-made infant formula, man-made hydrolyzed infant formula (partially or extensively), or man-made nutritional compositions in general. Such compositions may be embodiments of the invention.

Such compositions may be used in the indicated dosage as a nutritional solution or medicament to induce oral tolerance, especially to milk proteins. Such compositions may be administered to infants or sub-population of infants presenting symptoms or susceptibility to allergies. Such induction of oral tolerance may induce relief of allergies in the medium term (during the treatment or within 1, 6, 12 or 18 months after the treatment). Alternatively or additionally, the oral tolerance may be induced with positive effect later in life (e.g. 24, 36, 48, 72 months after the treatment), especially when the immune system has matured.

Dosage

According to one embodiment of the invention, the dose of peptide(s) is in the range of 0.4-50 umol/per kg bodymass/day, preferably from 0.9-40 umol/per kg bodymass/day. For example, if the peptides are administered as part of an infant formula, the peptides may be present in the formula at a concentration of 50-150 ug/g powder. A typical dosage of infant formula for an infant of five month-old baby would be three bottles per day of seven scoops of powder each, and for a six month-old baby or older, two bottles per day of seven scoops each. The doses are based on an average baby weight for a six-month-old being about 8 kg, and for a twelve-month-old being about 9.5 kilos.

Administration Period

The period of administration of the peptides of the invention can be continuous or discontinuous. Continuous administration is preferred for a more sustained effect. However, it is speculated that a discontinuous pattern (for example, daily administration during one week per month, or during alternate weeks) can induce positive effects on the young mammal or adult.

According to one embodiment of the invention, in young mammals who have not yet been exposed to BLG ("naive subjects") it is speculated that a "one-shot dose" of the peptide or a combination of peptides of the invention may suffice to induce oral tolerance to BLG. More generally, a longer duration is recommended, for example, daily administration during one to three weeks.

In young mammals that have already been exposed to BLG, a longer period of administration is preferred. In general, while positive effects are expected with relatively short duration of administration (for example, daily administration during one to four weeks), longer durations are believed to provide enhanced effect (for example, a duration of three to six months in humans, and corresponding periods in other mammals).

For adults who are already allergic to BLG, an administration period of at least one month may be required to carry out the "desensitization".

Preferably, the administration is by daily intake (to be taken once or twice a day), or by weekly intake (to be taken four or three times or twice or once a week).

Administration with Other Compounds

The peptides can be administered alone (pure or diluted in water or milk, including human breast milk for example) or in a mixture with other compounds (such as dietary supplements, nutritional supplements, medicines, carriers, flavours, digestible or non-digestible ingredients).

The peptides may be administered for example to a young infant, as part of a composition that is a human milk fortifier, or other nutritional supplement. If the peptides are to be administered to adults, they may be administered as a part of a food, drink or dietary supplement. The peptides may also be administered to all subjects (young mammals or adults alike) in a pharmaceutical composition.

According to one embodiment of the invention, the peptides may be added to, or be comprised into a base composition that is a hypoallergic composition intended for mammals, particularly human and pets. Thus, the base formula to which the peptides are added, or in which the peptides may be contained, may be a hypoallergenic (HA) formula in which the milk proteins are partially hydrolyzed, or a non-allergenic formula in which the milk proteins are extensively hydrolyzed or are replaced by free amino acids, or a cow milk substitute such as soya based. It may for example be an infant formula, a follow-up formula, or a nutritional composition for children with particular physiological/pathological conditions.

In one embodiment, the base formula is an elemental infant formula and the base formula comprises no peptides or proteins but only amino acids. In one embodiment the proteins of the base formula originate, in part or in full, from sweet whey from which the cGMP have been removed. Reference is made in that regard to EP880902 whereby a process allows the removal of practically all the caseino-glyco-macropeptide (a fraction rich in threonine and poor in tryptophan) from bovine whey thereby increasing the alpha-lactalbumin proportion (a fraction very rich in tryptophan). By combining this modified sweet whey fraction with skim milk, and with the addition of some free L-histidine and L-arginine (in order to reach the minimum amounts of these amino acids required by EC Directive), the formulation according to the invention has an amino acid profile much closer to that of human milk, characterised in particular by comparable tryptophan and threonine levels, allowing the adaptation of its protein content to that of human.

When administered together with the above described optimized protein profile, it is understood that the peptides can act synergistically with the optimized protein to deliver both the induction of oral tolerance while provide the optimized protein nutritional value (that may boost the effect of the peptides by fulfilling the protein needs in the most proper quantitative way).

When administered with elemental amino-acids, is it understood that the effect of the peptides is not masked or inhibited by the presence of potentially allergy-inducing proteins.

The peptides may be administered, for example, as part of an infant formula at a concentration of 50-150 ug/g powder.

The base hypoallergenic composition to which the peptides are added may contain as a source of nitrogen, peptides or free amino acids and, particularly from milk proteins, from cow or goat or sheep, such as whey proteins, alpha-lactalbumin, β-lactoglobulin, bovine serum albumin, casein acid, caseinates, or alpha, beta, kappa-casein, for example. The source of nitrogen can provide at least 7 to 25% of the total energy.

Vitamins and minerals are examples of typical dietary supplements. In a preferred embodiment, the composition is administered together with other compounds that enhance the described effect on the immunity of the young mammal or allergic adult. Such compounds can be other active compounds that synergistically or separately influence the immune response of the infant and/or potentiate the effect of the peptides, such as probiotics and prebiotics.

Examples of known probiotic compounds are *Bacillus, Bifidobacterum, Lactobacillus Saccharomyce, Streptococcus thermophilus, E. Faecium, E. Coli Nissle*. In particular, probiotics and non-replicating probiotics, such as the genus *Lactobacillus, Bifidobacterium* or combination thereof, for example *Lactobacillus paracasei, Lactobacillus GG, Lactobacillus rhamnosus, Bifidobacterium longum, Bifidobacterium lactis, Bifidobacterium breve*, or combination thereof, and applications of these bacteria.

Examples of known prebiotic compounds are carbohydrate compounds selected from the group consisting of inulin, fructooligosaccharide (FOS), short-chain fructooligosaccharide (short chain FOS), galacto-oligosaccharide (GOS), xylooligosaccharide (XOS), glangliosides, partially hydrolyzed guar gum (PHGG), acacia gum, soybean-gum, or mixtures thereof. Other carbohydrates may be present such as a second carbohydrate acting in synergy with the first carbohydrate and that is selected from the group consisting of xylooligosaccharide (XOS) gum, acacia gum, starch, partially hydrolyzed guar gum or mixtures thereof. The carbohydrate or carbohydrates may be present at about 1 g to 20 g or 1% to 80% or 20% to 60% in the daily doses of the composition. Alternatively, the carbohydrates are present at 10% to 80% of the dry composition.

In one embodiment the base formula or the final nutritional composition comprises a mix of oligosaccharide according to WO2007/090894 (general teaching and specifically example 1). It may be in particular used in combination with GOS. The base formula may provide an oligosaccharide mixture which comprises 5-70 wt % of at least one N-acetylated oligosaccharide selected from the group comprising GalNAcα1,3Galβ1,4Glc and Galβ1,6GalNAcα1,3Galβ1,4Glc, 20-90 wt % of at least one neutral oligosaccharide selected from the group comprising Galβ1,6Gal, Galβ1,6Galβ1,4Glc Galβ1,6Galβ11,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc and Galβ1,3Galβ1,3Galβ1,4Glc and 5-50 wt % of at least one sialylated oligosaccharide selected from the group comprising NeuAcα2,3Galβ1,4Glc and NeuAcα2,6Galβ1,4Glc.

In one embodiment the mixture (of the base formula or of the final nutritional composition) comprises 10-70 wt % of the specified N-acetylated oligosaccharide(s), 20-80 wt % of the specified neutral oligosaccharide(s) and 10-50 wt % of the specified sialylated oligosaccharide(s). More preferably the mixture comprises 15-40 wt % of the N-acetylated oligosaccharide(s), 40-60 wt % of the other neutral oligosaccharide(s) and 15-30 wt % of the sialylated oligosaccharide(s). A particularly preferred mixture is 30 wt % of the N-acetylated oligosaccharide(s), 50 wt % of the neutral oligosaccharide(s) and 20 wt % of the sialylated oligosaccharide(s).

Alternatively, the mixture may conveniently comprise 5-20 wt % of the specified N-acetylated oligosaccharide(s), 60-90 wt % of the specified neutral oligosaccharide(s) and 5-30 wt % of the specified sialylated oligosaccharide(s).

The oligosaccharide mixture of the invention may be prepared from one or more animal milks. The milk may be obtained from any mammal, in particular from cows, goats, buffalos, horses, elephants, camels or sheep.

Alternatively the oligosaccharide mixture may be prepared by purchasing and mixing the individual components. For example, synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc and mixtures thereof are commercially available under the trade marks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetyl-hexosamine containing oligosaccharide as described in Wrodnigg, T. M.; Stutz, A. E. (1999) Angew. Chem. Int. Ed. 38:827-828.

The sialylated oligosaccharides 3'sialyl-lactose and 6'sialyl-lactose may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

In a preferred aspect of the invention, the oligosaccharide mixtures described above are incorporated into a food product. In the context of the present invention, the term "food product" is intended to encompass any consumable matter. Hence, it may be a product intended for consumption by humans, in particular infant formula, follow-up formula, baby food such as infant cereals and the like. In particular, the oligosaccharide mixtures of the invention can be incorporated into infant formulas, dehydrated milk or cereal mixtures.

The Oligosaccharides above described present the advantageous effect to boost the immune conditions (up-regulation or down-regulation) of the subject in a way that makes it more receptive to the induction of oral tolerance induced by the peptides. That boost can be direct on the immune system or inflammation pathways or can be mediated by gut probiotics that are selectively promoted by the oligosaccharides.

One or more essential long chain fatty acids (LC-PUFAs) may be included in the composition. Examples of LC-PUFAs that may be added are docosahexaenoic acid (DHA) and arachidonic acid (AA). The LC-PUFAs may be added at concentrations so that they constitute greater than 0.01% of the fatty acids present in the composition.

One or more food grade emulsifiers may be included in the nutritional composition if desired; for example diacetyl tartaric acid esters of mono- and di-glycerides, lecithin and mono- or di-glycerides or a mixture thereof. Similarly suitable salts and/or stabilisers may be included. Flavours can be added to the composition.

The peptides may be incorporated into or be present in a composition that is an infant "preterm formula" for infants born before term or has a low birth weight, a "starter formula" or a "follow-on formula". An example of such starter formula is given in Example 3.

Example 1: Isolation and Identification of Peptides Capable of Inducing Oral Tolerance to BLG Cell Culture To assess MHC receptor expression on two different human monocytic cells (U937 and Thp1), cells were stained with APC conjugated anti HLA-DR (Santa Cruz Biotechnologies, clone L243) for 30 min on ice, washed twice with cold PBS 1× (Sigma) supplemented with 0.5% of FCS (Amimed, Bioconcept), then analyzed on a flow analyzer BD Fortessa (BD).

To assess the toxicity of BEBA-HA infant formula on U937 and Thp1 cell lines, cells were incubated with various concentrations of BEBA-HA product ranging from 10 mg to 1 ng reconstituted in complete RPMI1640 medium. Cells were incubated at a concentration of $1 \times 10^6$ cells/mL in 24 well plates for 24 h at 37° C. in presence of 5% $CO_2$. Cells were spun down and washed twice with PBS 1× supplemented with 0.5% of FCS, then stained with PE Annexin V Apoptosis Detection Kit I (BD Pharmingen). Finally, cells were analyzed by flow cytometry on a BD Fortessa (BD). The results demonstrated that BEBA-HA was not toxic to the cells at the doses used in the experiments.

The Thp1 and U937 cells were incubated in 20 mL RPMI-1640 medium with L-Glutamine (Sigma) supplemented with 10% heat-inactivated FCS (Amimed, Bioconcept) and Penicillin/Streptomycin (Sigma) at a concentration of $1 \times 10^6$ cells/mL in a T175 $cm^2$ (Falcon) with respectively 1 ug/mL and 100 ug/mL of BEBA-HA (Nestlé, Lot# L02680742AP) for a 24 hours period at 37° C. in presence of 5% $CO_2$. Cells were spun down and harvested to perform immunoprecipitation of MHC-peptide complexes.

Protein Lysate and Immunoprecipitation

Briefly, for each condition tested (control without BEBA-HA, sample with BEBA-HA for both cell lines), $2 \times 10^7$ cells were resuspended in ice cold TBS and washed three times. Cell pellet was then resuspended in lysis buffer containing 1% CHAPS and proteinase inhibitors. After lysis, the supernatant was collected and mixed with antibody-PAS beads that were previously prepared by incubating 60 ul of PAS beads with 50 ug of MHC II monoclonal antibody specific for HLA-DR molecules (Clone L243). Lysate and Ab-beads were incubated overnight at 4° C. with gentle rotation. Following affinity capture, beads were spun down and the supernatant discarded. Several washes were performed using respectively: 1×1 ml 1% CHAPS buffer, 1×1 ml 20 mM Tris/150 mM NaCl, 1×1 ml 20 mM Tris pH 8.0. After washing, 200 ul of 10% acetic acid solution was added to the beads, vortexed gently and incubated for 15 min at 70° C. Beads were spun down 5 min at 14000 g. This step was repeated once. Both supernatants were pooled and filtrated using a 10 kDa cut-off (Amicon Ultra, Millipore). Both the retentate (containing mainly HLA-DR antibodies and HLA-DR molecules) and the filtrate (containing HLA-DR presented peptides) were kept at 20° C. for further LC-MS/MS analysis.

MS Analysis

Before MS analysis, HLA-DR peptides were desalted using either reversed-phase C18 (The Nest group, USA) or mixed-mode OASIS (Waters, USA) desalting columns as described in the manufacturer's manual. After desalting, peptides were analyzed by nano-LC-MSMS using an in-house Magic C18 column (150×0.075 mm) for peptide separation (2-35% Acetontril/0.1% formaic acid in 30 minutes) coupled to an Orbitrap XL instrument. Peptides were selected for fragmentation using data-dependent acquisition of top five ions per each full scan. Dynamic exclusion was turned on with exclusion duration of 30 seconds. Fragmentation was performed using Collision Induced Dissociation (CID) at 35% collision energy. Peptides were finally identified by Sequest database search against a bovine milk database and manually validated based on spectrum quality and score.

Example 2: BLG-specific Humoral Immune Responses in Mice Gavaged with nBLG or Synthetic Peptides and then Experimentally Sensitized Mice Specific pathogen-free (SPF) BALB/cJ mice (3 to 4 weeks-old females, Centre d'Elevage René Janvier, Le Genest Saint-Isle, France) were housed in filtered cages under normal SPF husbandry conditions (autoclaved bedding and sterile water) and were acclimatized for two weeks before experiments. They were maintained on a diet deprived of animal protein, and in which BLG was not detected using specific sandwich immunoassays. All animal experiments were performed according to European Community rules of animal care, and with authorization 91-368 of the French Veterinary Services. All experiments were covered by agreement No. 2009-DDSV-074 (Oct. 29, 2009) from the Veterinary Inspection Department of Essonne (France).

Effect of BLG and Synthetic Peptide Administration

Groups of 6 or 7 mice were administered either 4 mg of native bovine BLG, or equivalent quantity (i.e. 0.22 µmole) of isolated synthetic BLG peptides. Either 0.6 mg of synthetic peptide (84-106), corresponding to the bovine BLG sequence numbers 84-106 (MW 2731 Da), or 2 mg of synthetic peptide (25-107) corresponding to the bovine BLG sequence numbers 25-107 (MW 9440 Da), were administered (n=7/group). Nine control mice received PBS. The synthetic peptides (25-107) and (84-106) were diluted in PBS. Administrations were performed on Days 1, 2, 3, 8, 9 and 10 by means of intra-gastric gavage using an animal feeding needle (Popper & sons, NY). Control mice received PBS (negative control mice, n=16). All mice were then sensitized on Day 14 by i.p. administration of 5 µg of native bovine BLG adsorbed on alum (Alhydrogel 3%, Superfos, Danemark, 1 mg/mouse).

The efficacy of mice sensitization was assessed by quantitative measurements of BLG-specific IgE antibodies on individual serum samples collected from the mice retro-orbital venous plexus under light anaesthesia (Isoflurane, Baxter) between days 30-33. Non-specific binding was determined using individual sera from 10 naive mice, and was deduced from the absorbance values measured with immune sera.

Statistical analysis using an unpaired t test with Welch's correction revealed a significant difference for BLG-specific IgE antibody concentrations between mice receiving peptide (25-107) and PBS group (p=0.04) (see FIG. 1).

Statistical Analysis

All statistical analyses were performed using GraphPad Prism version 4.00 for Windows (GraphPad Software, San Diego, Calif., USA). Normality distribution was first examined using Shapiro-Wilk normality test before analysis of the statistical significance with one-way ANOVA and Tukey's multiple comparison post-test. When data were not normally distributed, a non-parametrical test was performed, using Kruskal-Wallis test followed by Dunn's multiple comparison test (DMCT). Differences between groups were regarded as significant when p<0.05. Comparison of two specific groups was performed using unpaired t-test with Welch's correction on log-transformed data that allows obtaining comparable variance.

Example 3

An example of the composition of an infant formula for use according to the present invention is given below. This composition is given by way of illustration only.

| Nutrient | Per 100 kcal | Per litre |
| --- | --- | --- |
| Energy | 100 | 670 |
| Partially Hydrolyzed Protein including peptides 1-5 | 1.83 | 12.3 |
| Fat | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (100% GOS) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| *Lactobacillus* GG | $2 \times 10^7$ cfu/g of powder | |

The invention claimed is:

1. A method for inducing oral tolerance to a milk protein from at least one of cow, sheep, buffalo or goat in a mammal, the method comprising administering to the mammal at least one peptide having an amino acid length from five to twelve amino acids and comprising a sequence selected from the group consisting of SEQ ID No. 1-5, the at least one peptide is administered at a dose between 0.4-50 μmol/per kg bodymass/day.

2. The method according to claim 1 wherein the at least one peptide is combined with one or more other peptides having an amino acid length from five to twelve amino acids and comprising a sequence selected from the group consisting of a, b and c.

3. The method according to claim 1, wherein the mammal is a human infant.

4. The method according to claim 1, wherein the at least one peptide consists of two or more peptides.

5. The method according to claim 1, wherein the at least one peptide is of milk origin.

6. The method according to claim 1, wherein the at least one peptide is present as (i) isolated peptidic fractions from hydrolysis of proteinaceous material containing the milk protein and/or (ii) one or more synthetically prepared peptides.

7. The method according to claim 1, wherein the at least one peptide downregulates IgE expression in the mammal upon previous, concomitant or sub sequent β-lactoglobulin sensitization.

8. The method according to claim 1, wherein the at least one peptide is administered at an interval selected from the group consisting of every day, every second day, every third day, once a week for a period of at least one week, once a week for a period of at least one month, and once a week for a period of at least three months.

9. The method according to claim 1, wherein the mammal is selected from the group consisting of (i) an infant or child at risk of developing allergy to cow's milk and (ii) a human adult allergic to cow's milk.

10. The method according to claim 1, wherein the mammal is a companion animal.

11. The method according to claim 1, wherein the at least one peptide is administered in a form selected from the group consisting of (i) a pure form, (ii) a dilution in water or human breast milk, and (iii) added to or contained in a composition that is a nutritional supplement, a human milk fortifier, or an infant formula.

12. The method according to claim 11, wherein the composition is a "non-allergenic" or hypoallergenic composition.

13. The method according to claim 12, wherein the "non-allergenic" or hypoallergenic composition is a starter infant formula, a follow-up infant formula or a growing up milk.

14. The method according to claim 1, wherein the at least one peptide is administered in a composition comprising between 25-250 µg of peptide per gram of dry composition.

15. The method according to claim 1, wherein the at least one peptide is administered in a composition that comprises further ingredients selected from the group consisting of inulin, fructooligosaccharide (FOS), short-chain fructooligosaccharide (short chain FOS), galacto-oligosaccharide (GOS), xylooligosaccharide (XOS), ganglioside, partially hydrolyzed guar gum, acacia gum, soybean-gum, and mixtures thereof.

16. The method according to claim 11, wherein the composition comprises probiotics.

17. A method for inducing oral tolerance to cow's, buffalo's or goat's milk proteins in a mammal, the method comprising administering to the mammal a composition comprising at least one peptide selected from the group of sequences consisting of SEQ ID No. 1-5, the at least one peptide is administered at a dose between 0.4-50 µmol/per kg bodymass/day.

18. The method according to claim 17, wherein the cow's, buffalo's or goat's milk protein is β-lactoglobulin.

* * * * *

SEQUENCE LISTING

```
<160> NUMBER OF SEQ ID NOS: 6

<210> SEQ ID NO 1
<211> LENGTH: 6
<212> TYPE: PRT
<213> ORGANISM: Bos taurus

<400> SEQUENCE: 1
```

-continued

```
Ile Val Thr Gln Thr Met
1               5

<210> SEQ ID NO 2
<211> LENGTH: 7
<212> TYPE: PRT
<213> ORGANISM: Bos taurus

<400> SEQUENCE: 2

Lys Gly Leu Asp Ile Gln Lys
1               5

<210> SEQ ID NO 3
<211> LENGTH: 8
<212> TYPE: PRT
<213> ORGANISM: Bos taurus

<400> SEQUENCE: 3

Asp Ala Gln Ser Ala Pro Leu Arg
1               5

<210> SEQ ID NO 4
<211> LENGTH: 9
<212> TYPE: PRT
<213> ORGANISM: Bos taurus

<400> SEQUENCE: 4

Val Glu Glu Leu Lys Pro Thr Pro Glu
1               5

<210> SEQ ID NO 5
<211> LENGTH: 5
<212> TYPE: PRT
<213> ORGANISM: Bos taurus

<400> SEQUENCE: 5

Ile Ile Ala Glu Lys
1               5

<210> SEQ ID NO 6
<211> LENGTH: 7
<212> TYPE: PRT
<213> ORGANISM: Bos taurus

<400> SEQUENCE: 6

Ala Leu Pro Met His Ile Arg
1               5
```